(12) United States Patent
Berger et al.

(10) Patent No.: US 9,084,681 B2
(45) Date of Patent: Jul. 21, 2015

(54) SPINE DISC REPLACEMENT WITH COMPLIANT ARTICULATING CORE

(75) Inventors: Roger Berger, Oberdorf (CH); Joern Richter, Oberforf (CH); David Koch, West Chester, PA (US); Markus Kraft, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 33 days.

(21) Appl. No.: 13/162,954

(22) Filed: Jun. 17, 2011

(65) Prior Publication Data

US 2012/0022652 A1   Jan. 26, 2012

Related U.S. Application Data

(60) Provisional application No. 61/356,226, filed on Jun. 18, 2010.

(51) Int. Cl.
*A61F 2/44* (2006.01)
*A61F 2/46* (2006.01)
*A61F 2/30* (2006.01)

(52) U.S. Cl.
CPC .............. *A61F 2/4425* (2013.01); *A61F 2/4611* (2013.01); *A61F 2002/30009* (2013.01); *A61F 2002/30014* (2013.01); *A61F 2002/30448* (2013.01); *A61F 2002/30581* (2013.01); *A61F 2002/30583* (2013.01); *A61F 2002/30586* (2013.01); *A61F 2002/30588* (2013.01); *A61F 2002/30677* (2013.01); *A61F 2002/30841* (2013.01); *A61F 2310/00017* (2013.01); *A61F 2310/00023* (2013.01); *A61F 2310/00179* (2013.01)

(58) Field of Classification Search
USPC ............................................ 623/17.11–17.16
See application file for complete search history.

(56) References Cited

U.S. PATENT DOCUMENTS

| | | | | |
|---|---|---|---|---|
| 5,562,736 | A | * | 10/1996 | Ray et al. ..................... 606/86 A |
| 5,755,797 | A | * | 5/1998 | Baumgartner ............. 623/17.16 |
| 6,187,329 | B1 | * | 2/2001 | Agrawal et al. ............... 424/426 |
| 6,544,287 | B1 | | 4/2003 | Johnson et al. |
| 6,620,162 | B2 | | 9/2003 | Kuslich et al. |
| 6,869,445 | B1 | * | 3/2005 | Johnson ..................... 623/17.11 |
| 2002/0147497 | A1 | * | 10/2002 | Belef et al. ................. 623/17.12 |
| 2003/0083746 | A1 | | 5/2003 | Kuslich |
| 2004/0024463 | A1 | | 2/2004 | Thomas et al. |
| 2005/0209595 | A1 | * | 9/2005 | Karmon .......................... 606/76 |
| 2006/0036241 | A1 | | 2/2006 | Siegal |
| 2006/0052874 | A1 | | 3/2006 | Johnson et al. |
| 2006/0259144 | A1 | * | 11/2006 | Trieu ........................ 623/17.13 |
| 2006/0276887 | A1 | * | 12/2006 | Brady et al. .................. 623/1.53 |
| 2006/0282164 | A1 | | 12/2006 | Seastrom |
| 2007/0005140 | A1 | | 1/2007 | Kim et al. |
| 2007/0038301 | A1 | * | 2/2007 | Hudgins .................... 623/17.16 |
| 2007/0162135 | A1 | | 7/2007 | Segal et al. |

(Continued)

FOREIGN PATENT DOCUMENTS

| | | |
|---|---|---|
| EP | 0621020 A1 | 10/1994 |
| EP | 1212992 A2 | 6/2002 |

(Continued)

*Primary Examiner* — Christian Sevilla
(74) *Attorney, Agent, or Firm* — Baker & Hostetler LLP

(57) ABSTRACT

An intervertebral implant can include a pair of endplates between which is coupled a bag that is filled or is fillable with small beads or particles having smooth exterior geometries. The bead sack implant allows for articulation about various centers of rotation without a predefined neutral position.

20 Claims, 9 Drawing Sheets

(56) References Cited

U.S. PATENT DOCUMENTS

| | | |
|---|---|---|
| 2007/0203579 A1 | 8/2007 | Vittur et al. |
| 2008/0009792 A1 | 1/2008 | Henniges et al. |
| 2008/0021556 A1* | 1/2008 | Edie .......................... 623/17.11 |
| 2008/0154305 A1 | 6/2008 | Foley et al. |
| 2008/0306595 A1 | 12/2008 | McLeod et al. |
| 2009/0030525 A1 | 1/2009 | Desrosiers et al. |
| 2009/0105826 A1 | 4/2009 | McLeod et al. |
| 2009/0248159 A1 | 10/2009 | Aflatoon |
| 2009/0326657 A1 | 12/2009 | Grinberg et al. |

FOREIGN PATENT DOCUMENTS

| | | | |
|---|---|---|---|
| WO | WO 00/59412 A1 | 10/2000 | |
| WO | WO 2007/140315 A2 | 12/2007 | |
| WO | WO 2007140315 A2 * | 12/2007 | ............. A61B 17/88 |
| WO | WO 2011/159999 A1 | 12/2011 | |

* cited by examiner

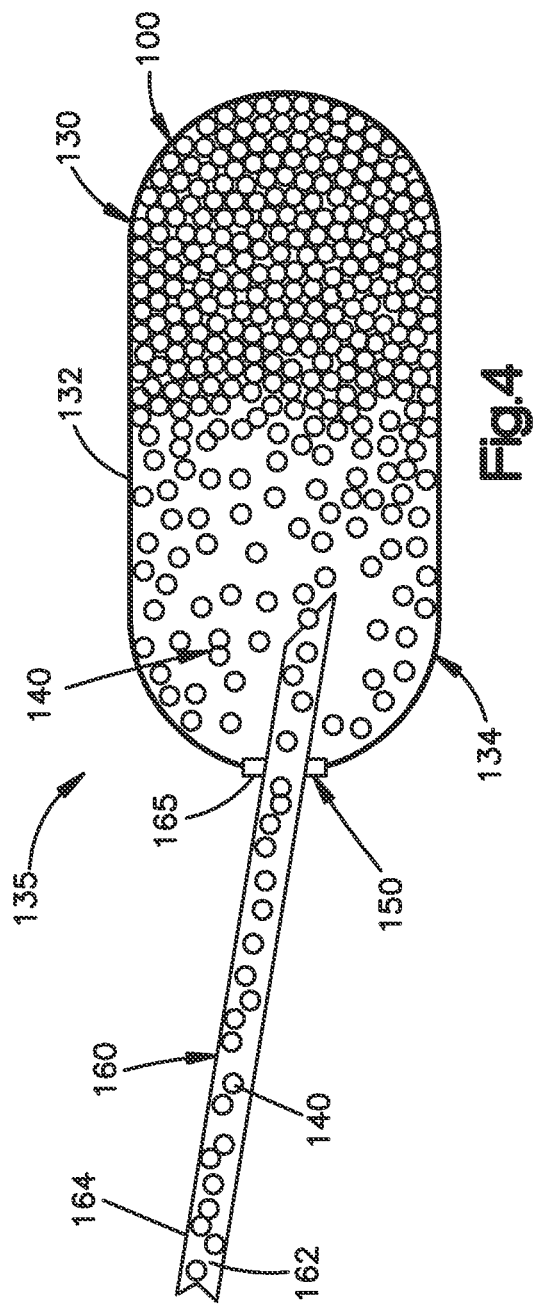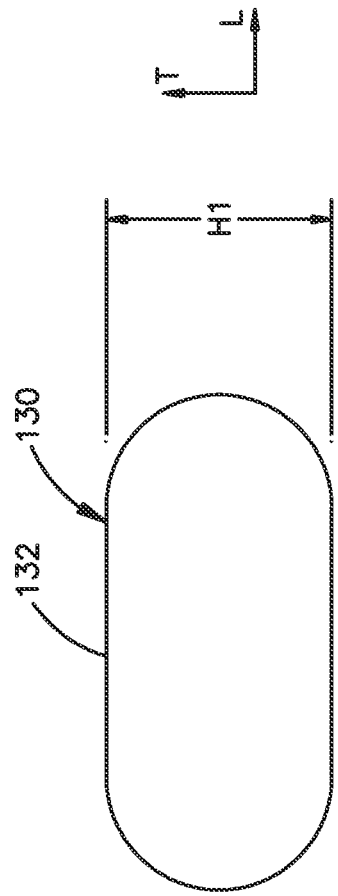

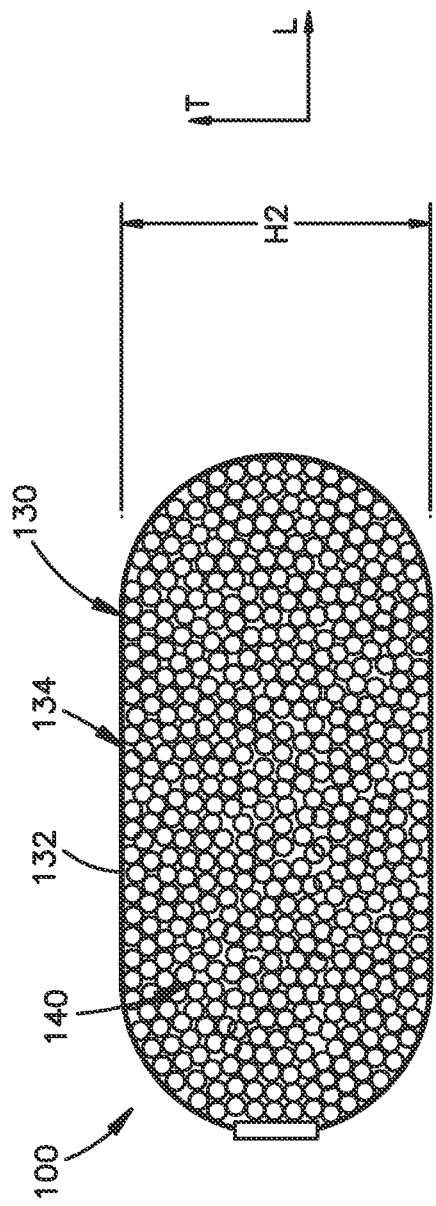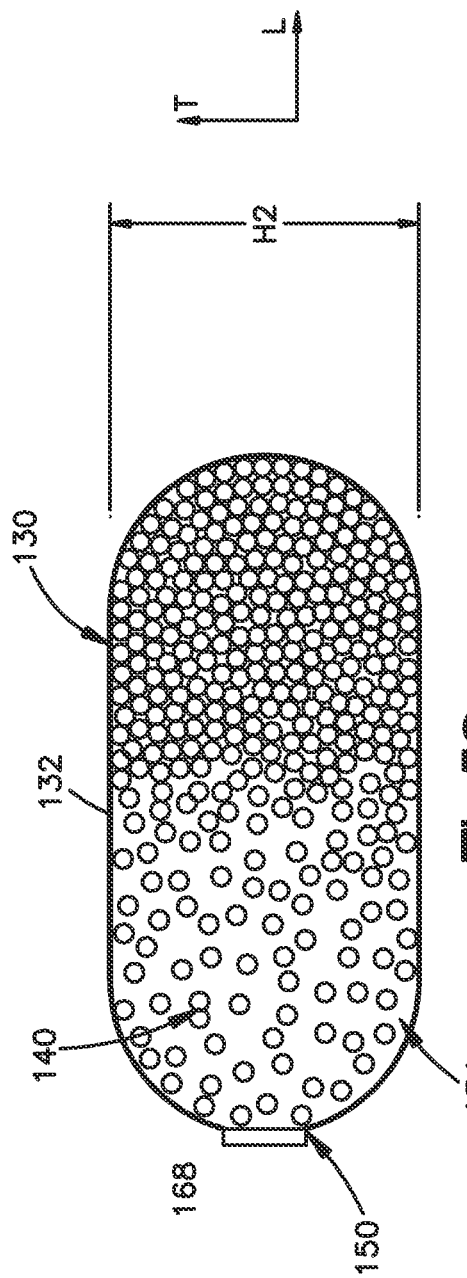

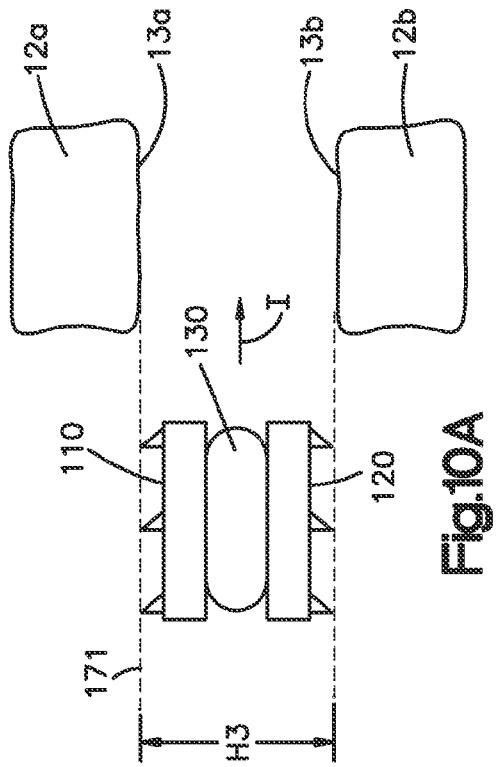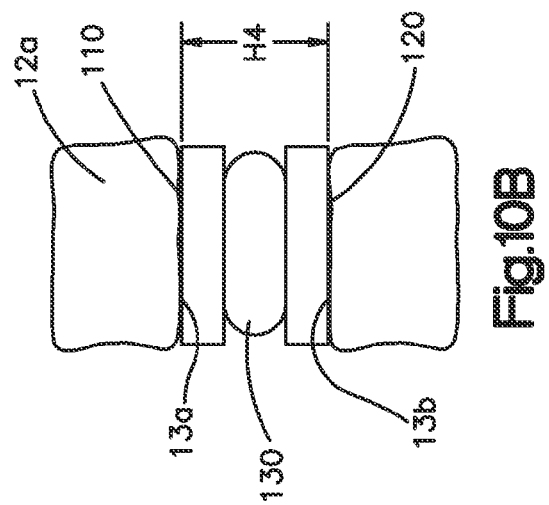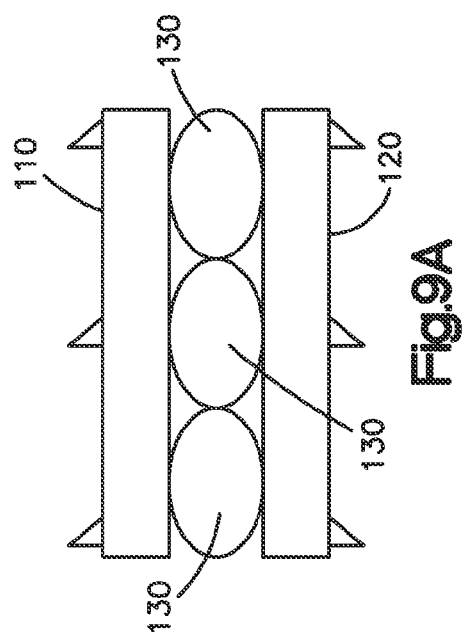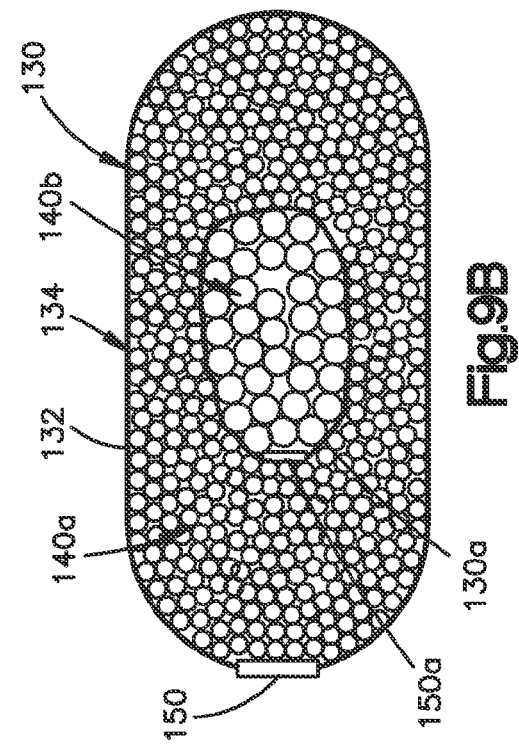

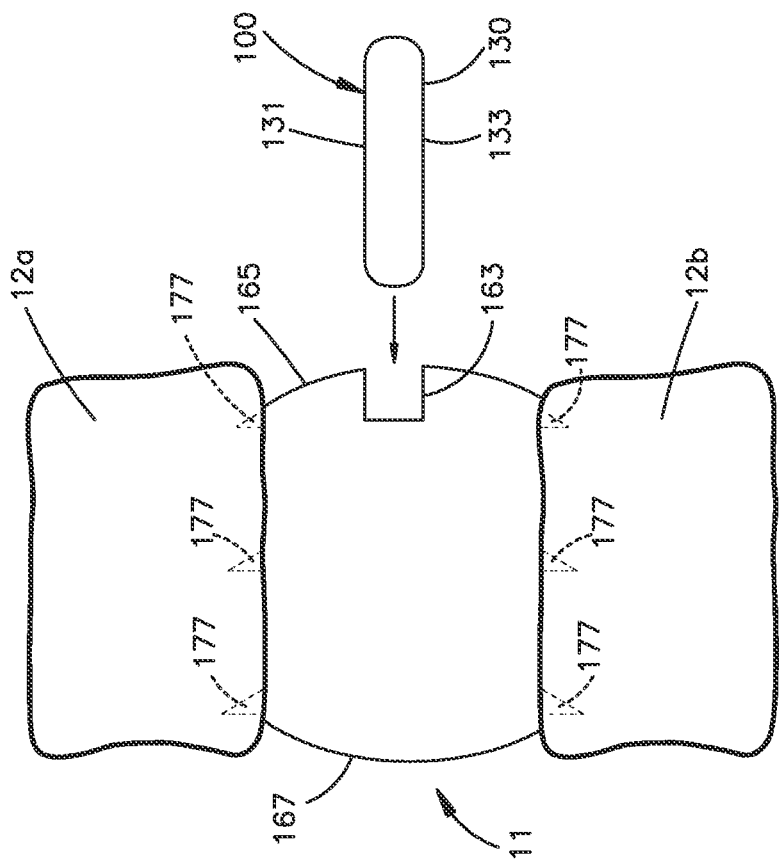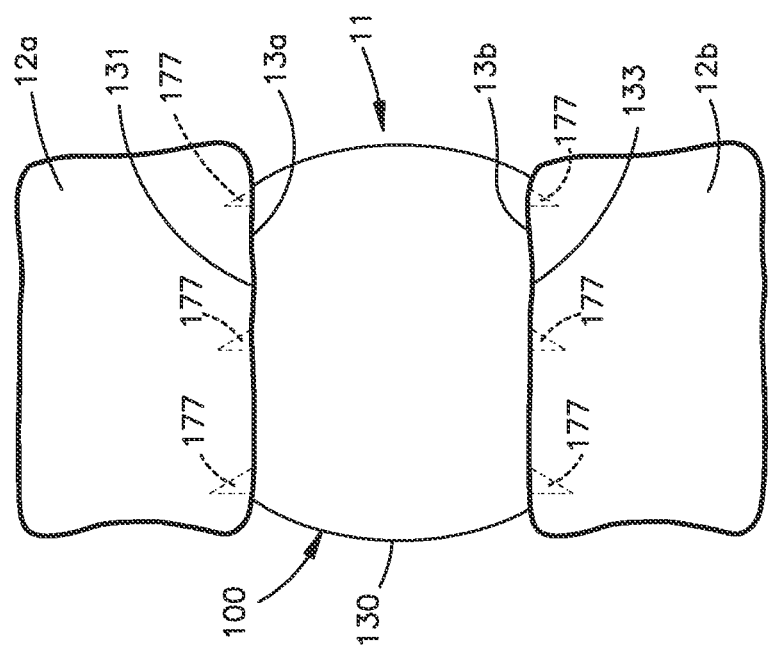

SPINE DISC REPLACEMENT WITH COMPLIANT ARTICULATING CORE

CROSS-REFERENCE TO RELATED APPLICATIONS

This applications claims priority to U.S. Provisional Patent Application Ser. No. 61/356,226, filed Jun. 18, 2010, the disclosure of which is hereby incorporated by reference as if set forth in its entirety herein.

BACKGROUND

Historically, complete removal of a disc from between adjacent vertebrae resulted in fusing the adjacent vertebrae together. This "spinal fusion" procedure, which is still in use today, is a widely accepted surgical treatment for symptomatic lumbar and cervical degenerative disc disease. More recently, disc arthoplasty has been utilized to insert an artificial intervertebral disc implant into the intervertebral space between adjacent vertebrae. Such implants have been inserted into lumbar, thoracic, and cervical intervertebral spaces between adjacent vertebral bodies through an anterior, antero-lateral (oblique), lateral, extraforaminal, transforaminal, or posterior surgical approach.

Such disc implants can provide for limited universal movement of the adjacent vertebrae with respect to each other. The aim of total disc replacement is to remove pain generation (caused by a degenerated disc), restore anatomy (disc height), and maintain mobility in the functional spinal unit so that the spine remains in an adapted sagittal balance. As a result, the trunk, legs, and pelvis are in equilibrium and can maintain harmonious sagittal curves and thus promote the damping effect of the spine.

One such intervertebral implant includes an upper part mounted to an adjacent vertebra, a lower part mounted to another adjacent vertebra, and a cavity located between the upper and lower parts. The cavity can be intraoperatively filled with organic, such as allograft, and/or synthetic, such as beta-tricalcium phosphate, bone graft substitutes to promote fusion between the implant and adjacent vertebra. More recently, the cavities of such implants have been pre-filled with a synthetic bone graft substitute prior to implantation into the intervertebral space. Such implants are often made from a metal, such as titanium, or polymer. During the implantation procedure, the vertebral bodies are distracted so as to expand the intervertebral space to a height that allows clearance for the insertion of the implant. Once the implant has been inserted, the distraction forces are released, thereby allowing the vertebral bodies to return to their resting position against the implant.

BRIEF SUMMARY

In accordance with one embodiment, an intervertebral implant is configured to be inserted into an intervertebral space that is disposed between a first vertebral body and a second vertebral body. The intervertebral implant includes a compliant bag that includes an outer wall that defines a superior surface configured to be disposed adjacent the superior vertebral body, and an inferior surface configured to be disposed adjacent the inferior vertebral body, and an internal void. The intervertebral implant further includes a plurality of fill particles configured to be disposed in the internal void, such that the compliant bag defines a first height before the fill particles are inserted into the internal void, and a second height after the fill particles are inserted into the internal void, wherein the second height is greater than the first height. The fill particles touch each other in the internal void such that the compliant bag provides a first resistance to relative rotation of the superior and inferior surfaces when the internal void has a first volume of fill particles, and the fill particles engage each other such that the compliant bag provides a second resistance to relative rotation of the superior and inferior surfaces, that is greater than the first resistance when the internal void includes a second volume of the fill particles that is greater than the first volume. Accordingly, the compliant bag provides resistance to relative rotation of the superior and inferior surfaces. The particles disposed in the bag can allow and resist relative motion of the superior and inferior surfaces in any direction as desired.

BRIEF DESCRIPTION OF THE SEVERAL VIEWS OF THE DRAWINGS

The foregoing summary, as well as the following detailed description of illustrative embodiments of the instrument of the present application, will be better understood when read in conjunction with the appended drawings. For the purposes of illustrating the lumbar spinal construct with total disc replacement implant of the present application, there is shown in the drawings illustrative embodiments. It should be understood, however, that the application is not limited to the precise arrangements and instrumentalities shown. In the drawings:

FIG. 4 is a side elevation view of an implant assembly including the intervertebral implant illustrated in FIG. 3 and an insertion instrument coupled to the intervertebral implant so as to inject fill particles into the internal void;

FIG. 5A is a side elevation view of the compliant bag illustrated in FIG. 3 prior to injection of fill particles into the internal void;

FIG. 5B is a side elevation view of the compliant bag illustrated in FIG. 5A after injection of the fill particles into the internal void;

FIG. 5C is a side elevation view of a the compliant bag similar to the compliant bag illustrated in FIG. 5A, but constructed in accordance with an alternative embodiment;

FIG. 9A is a side elevation view of an intervertebral implant including a pair of endplates and a plurality, for instance at least a pair, of compliant bags disposed between the endplates in accordance with another embodiment;

FIG. 9B is a side elevation of a compliant bag constructed in accordance with another embodiment;

FIG. 10A is a side elevation view showing the intervertebral implant illustrated in FIG. 2A inserted into an intervertebral space at a first height;

FIG. 10B is a side elevation view showing the intervertebral implant illustrated in FIG. 10A disposed in the intervertebral space at a second height that is greater than the first height;

FIG. 11A is a side elevation view of an intervertebral implant including a compliant bag implanted in an intervertebral space; and FIG. 11B is a side elevation view of an intervertebral implant including a compliant bag as it is implanted into an intervertebral disc;

DETAILED DESCRIPTION

Figure 1:
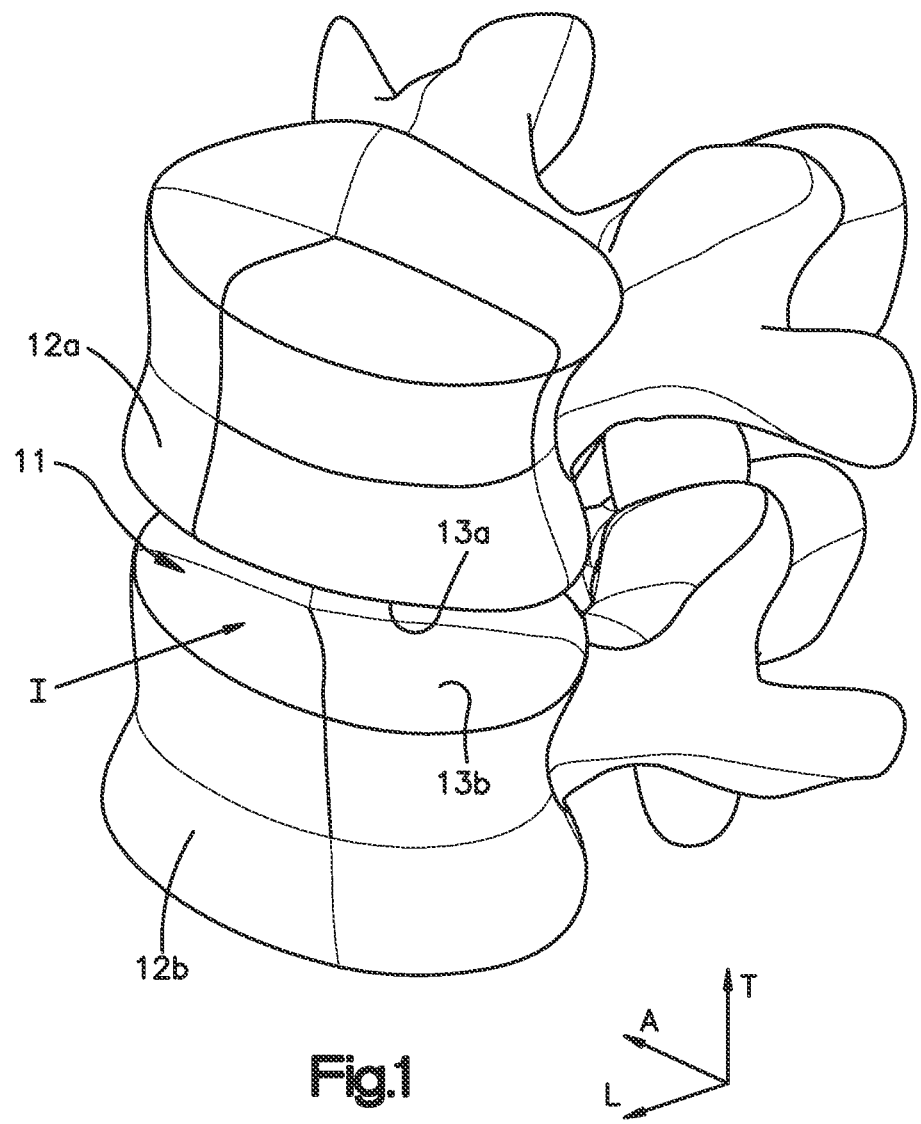
FIG. 1 is a perspective view of an intervertebral space defined between a superior vertebral body and an inferior vertebral body.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior", "superior," "inferior," "medial," "lateral," and related words and/or phrases are used to designate various positions and orientations in the human body to which reference is made and are not meant to be limiting. The terminology includes the above-listed words, derivatives thereof and words of similar import.

Referring to FIG. 1, an intervertebral space 11 is defined between a superior vertebral body 12a and an inferior vertebral body 12b. The superior vertebral body 12a defines a respective inner surface 13a, and the adjacent inferior vertebral body 12b defines a respective inner surface 13b. The inner surfaces 13a and 13b define the intervertebral space 11. Thus, the intervertebral space 11 is disposed between the vertebral bodies 12a and 12b. The vertebral bodies 12a and 12b can be anatomically adjacent vertebral bodies, for instance after a discectomy has been performed that has removed the intervertebral disk disposed in the intervertebral space 11. Alternatively or additionally, the vertebral bodies 12a and 12b can remain after a vertebral body has been removed from a location between the vertebral bodies 12a and 12b. In accordance with the illustrated embodiment, the intervertebral space 11 is defined after a discectomy, whereby the disc material has been removed or at least partially removed to prepare the intervertebral space 11 to receive an intervertebral disc implant, such as a total disc replacement (TDR) implant that can be inserted into the intervertebral space 11. The implant can define any height as desired such that when the implant is inserted into the intervertebral space 11, the implant can restore the height between the vertebral bodies 12a and 12b to the desired height. The intervertebral space 11 can be disposed anywhere along the spine as desired. Moreover, the superior vertebral body 12a may be considered a first or second vertebral body and the inferior vertebral body 12b may be considered a corresponding second or first vertebral body.

Figure 2A:
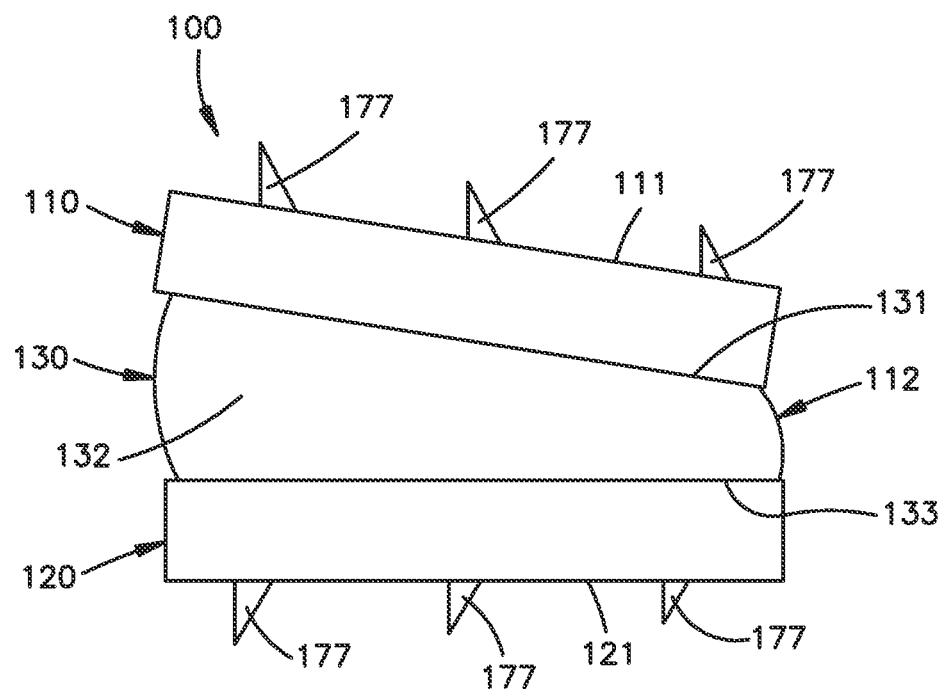
FIG. 2A is a side elevation view of an intervertebral implant constructed in accordance with one embodiment, including a pair of endplates and a compliant bag disposed between the endplates.
Figure 2B:
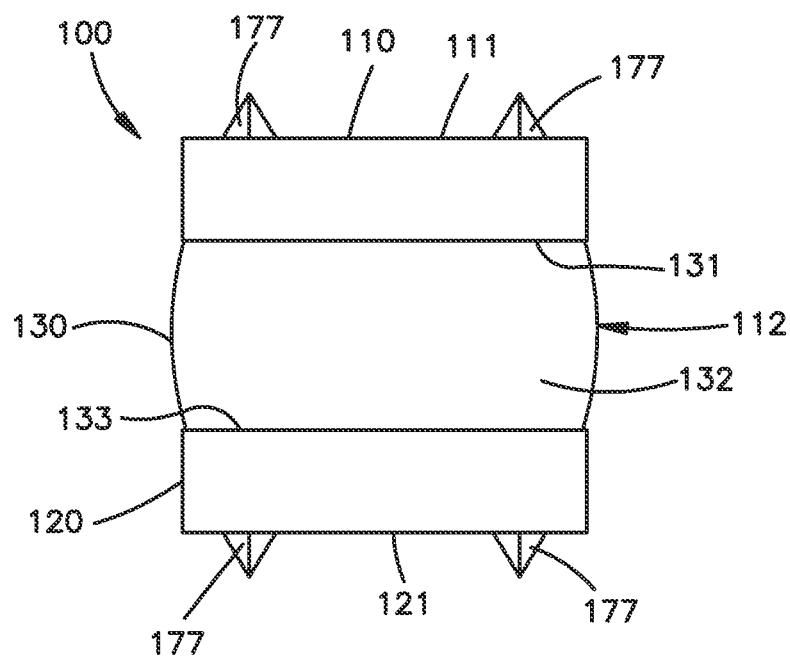
FIG. 2B is an anterior (end elevation) view of the intervertebral implant illustrated in FIG. 2A.
Figure 3:
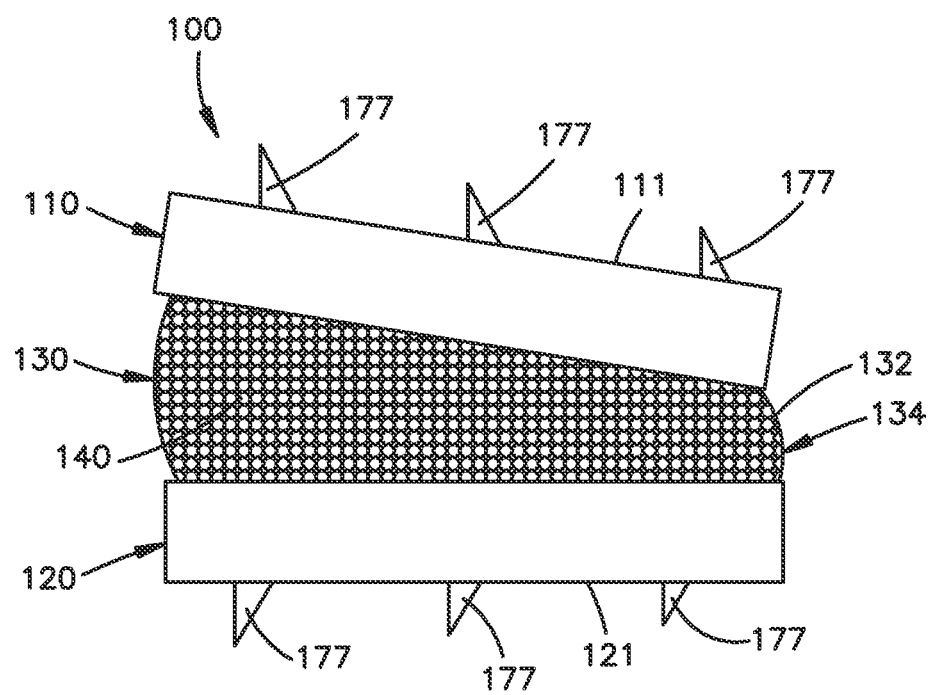
FIG. 3 is a side elevation view of the intervertebral implant illustrated in FIG. 2A, but with a wall removed so as to illustrate an internal void of the compliant bag that contains a plurality of fill particles.

Referring also to FIGS. 2A-3, an intervertebral implant 100, which can be a total disc replacement implant, can be inserted into the intervertebral space 11 along a longitudinal insertion direction I, which can be a posterior direction in accordance with the illustrated embodiment. The distractable intervertebral implant 10 is described herein as extending horizontally along a longitudinal direction "L" and lateral direction "A", and vertically along a transverse direction "T". Unless otherwise specified herein, the terms "lateral," "longitudinal," and "transverse" are used to describe the orthogonal directional components of various components. It should be appreciated that while the longitudinal and lateral directions are illustrated as extending along a horizontal plane, and that the transverse direction is illustrated as extending along a vertical plane, the planes that encompass the various directions may differ during use. For instance, when the intervertebral implant 100 is inserted into the intervertebral space 11 the transverse direction T extends generally along the superior-inferior (or caudal-cranial) direction, while the plane defined by the longitudinal direction L and lateral direction A lie generally in the anatomical plane defined by the anterior-posterior direction, and the medial-lateral direction. Accordingly, the directional terms "vertical" and "horizontal" are used to describe the distractable intervertebral implant 10 and its components as illustrated for the purposes of clarity and illustration.

The intervertebral implant 100 includes a first or superior endplate 110, a second or inferior endplate 120, and an implant body 112 that can be disposed between, and in accordance with the illustrated embodiment, connected between the superior endplate 110 and the inferior endplate 120. When the intervertebral implant 100 is inserted into the intervertebral space 11, the superior endplate 110 is configured to be disposed adjacent the superior vertebral body 12a, and thus can face and abut the inner surface 13a of the superior vertebral body 12a, and the inferior endplate 120 is configured to be disposed adjacent the inferior vertebral body 12b, and thus can face and abut the inner surface 13b of the inferior vertebral body 12b. The implant body 112 can be configured as a compliant bag 130 that includes an outer flexible bag wall 132 that defines an internal void 134, and a plurality of fill particles 140 disposed in the void 134. The compliant bag 130 define a first or superior outer surface 131 that can be attached to the first or superior endplate 110, and a second or inferior outer surface 133 that can be attached to the second or inferior endplate 120. The first and second outer surfaces 131 and 133 are spaced from each other along the transverse direction T, and the first and second endplates 110 and 120 are likewise spaced from each other along the transverse direction T.

The compliant bag 130 may be formed from a range of compliant or noncompliant biocompatible materials, such as at leas one or more of artificial soft tissue, metal, coretex-like materialst, plastics and polymers, woven fabrics, super elastic metal materials such NiTi alloys, artificial tissues, natural body tissues, and the like. In accordance with one embodiment, the compliant bag 130 can be prefilled with the fill particles 140. For instance, the compliant bag 130 can be formed around the fill particles. The bag 130 can be manufactured as desired. For instance, the bag 130 can be woven, knitted blown, cast, or any suitable alternative or manufactured using any combination of the above manufacturing techniques. The compliant bag 130 can define any geometry as desired, and for instance can be tailored to a specific clinical indication and configured for a specific anatomy. When the intervertebral implant 100 is configured to be used as a total disc replacement implant, the shape of the compliant bag 130 can be cylindrical, cubical, prismatic, pillow-shaped, kidney-shaped, doughnut-shaped, or any other suitable shape.

In accordance with one embodiment, as illustrated in FIG. 4, the compliant bag 130 can further define a port 150 that extends through the compliant bag wall 132 between the internal void 134 and the ambient environment, and is configured to receive the fill particles 140 that are inserted into the internal void 134 of the compliant bag 130. The fill particles 140 can be inserted through the port 150 and into the internal void 134, for instance interoperatively. An implant assembly 135 can thus include the intervertebral implant 100 and an insertion instrument 160 that is configured to introduce the fill particles 140 into the internal void 134 so as to increase the height of the bag 130 along the transverse direction from a first height H1 (see FIG. 5A) to a second height H2 (see FIG. 5B) that is greater than the first height H1. Thus, the compliant bag 130 can be referred to as an expandable bag. The port 150 can be integrated into the wall of the compliant bag 130, and can be positioned so as to be accessible by the insertion instrument 160 during surgery or even after the surgery via a percutaneous approach.

For instance, the insertion instrument 160 can be provided as a needle or cannula, and can thus include a substantially tubular body 162 that defines a channel 164. The insertion instrument 160 can be configured to mate with the port 150. Alternatively or additionally, the insertion instrument 160 can be configured to be inserted into the compliant bag 130, for instance at the port 150, without distorting the compliant bag 130. When a distal end of the insertion instrument 160 is mated with or inserted into the port 150, the channel 164 is placed in fluid communication with the internal void 134. The fill particles 140 can be introduced into the channel 164, for instance at a proximal end of the insertion instrument, and can travel into the internal void 134 of the compliant bag 130. After a desired volume of fill particles 140 has been introduced into the void 134, the insertion instrument 160 can be removed and the port 150 can be closed. For instance, the port 150 can be constructed as a one-way valve that includes one or more membranes 166 that are configured to self-seal after the insertion instrument 160 has been removed. Alternatively, the port 150 can be constructed as any suitable one-way valve known in the art. Alternatively still, as illustrated in FIG. 5C, the port 150 can include an opening that extends through the bag wall 132 and a cover 168 that can be opened so as to expose the internal void 134 to the ambient environment, and thus the channel 164 of the insertion instrument 160 when the insertion instrument is mated with the port 150. The cover 168 can subsequently be closed and secured to the wall 132 so as to seal the internal void 134 and prevent migration of the fill particles 140 out the internal void 134.

It should thus be appreciated that the port 150 can be opened so as to configured the internal void 134 to be placed into fluid communication with the insertion instrument (for instance, when the cover 168 is opened or when the insertion instrument is inserted through the port 150. Once the port 150 has been opened, the fill particles 140 can travel through the channel 164 of the insertion instrument and into the internal void 134. The port 150 can also be opened to remove at least some up to all of the fill particles 140 from the compliant bag 130 as desired, such that the fill particles 140 travel from the internal void 134, through the port 150, and into the insertion instrument 160. For instance, the implant assembly 135 can include a pump that is mated to the proximal end of the insertion instrument 160, which can also be referred to as a removal instrument, and can apply a vacuum force to the channel 164, which is communicated to the internal void 134 through the port 150. The vacuum force can draw the fill particles 140 from the internal void 134, through the port 150, and into the channel 164 of the instrument 160. For instance, it may be desired to remove fill particles 140 from the compliant bag 130 when too many fill particles 140 are disposed in the internal void 134, thereby producing a an undesired implant height, rigidity, or stiffness, or to reduce the size of the implant 100 in the case of a subsequent procedure, such as a revision or implant removal surgery.

Figure 6:
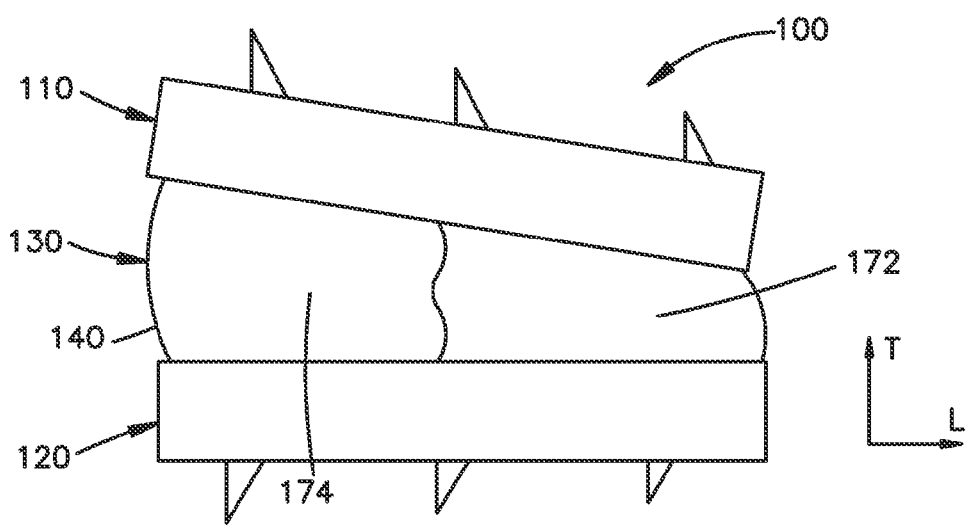
FIG. 6 is a side elevation view of the intervertebral implant illustrated in FIG. 2A, defining first and second regions.

Referring now to FIG. 6, the compliant bag 130 can define a plurality of regions, for instance at least first and second regions 172 and 174, that can have at least one different implant characteristic, which can include at least one or more of a strength, rigidity, and a flexibility. Thus, each of the regions 172 and 174 can define individual motion characteristics tailored such that the motion characteristics of the compliant bag 130 can provide a physiologically natural set of motion characteristics. Further, with the provision of a bag 130 having differing regional characteristics, the resulting motion of the implant 100 can be tailored to meet specific desired criteria, such as providing restriction to motion in a first direction and less restriction to motion in a second direction, for instance when the first region 172 is spaced from the second region 174 along the first direction, and the second region 174 is spaced from the first region 172 along the second direction, which can be opposite the first direction or angularly offset from the first direction. For instance, the first region 172 and second region 174 can be defined by orienting the material, such as fibers or fabrics, that comprise the compliant bag 130 in different directions relative to the desired motion that is being controlled. Alternatively, the first and second regions 142 and 144 can be made from different materials.

Figure 7:
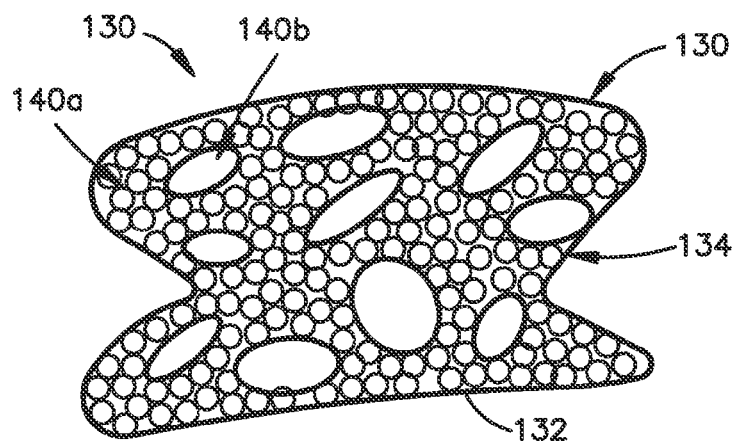
FIG. 7 is a side elevation view of the compliant bag of the intervertebral implant illustrated in FIG. 2A, including first and second different types of fill particles.

The fill particles 140 can be configured as beads or any independent rigid, semi rigid, or compliant elements having spheroid, ellipsoid, or other geometries whose exterior surfaces are smooth. The fill particles 140 can be formed from ceramics, metal, diamond-like materials, polymers, artificial bone, plastic, and the like. Some of the fill particles 140, such as the first type 140a, can be made from a first material, and some of the fill particles 140, such as the second type 140b, can be made from a second material the is different than the first material. In accordance with one embodiment, the plurality of fill particles 140 are homogenous in nature, though it should be appreciated in an alternative embodiment, for instance shown in FIG. 7, the fill particles 140 can include a plurality of different types of fill particles 140, such as at least first and second different types 140a and 140b of fill particles 140, disposed in the internal void 134. For instance, the first and second different types 140a and 140b of fill particles 140 can be have at least one different characteristic, which can include at least one or more of a size, different geometry, material, rigidity, and elasticity. Additionally, the bag 130 can contain a fluid that is disposed in the internal void 134. The fluid can occupy spaces between the fill particles 140. It should be further appreciated that the bag 130 can contain different types of fluids having at least one different characteristic, such as viscosity. The fill particles 140 can further include a mixture of different materials. For instance, the fill particles 140 can include a medication such as antibiotics in the compliant bag 130. The antibiotics can mix with bodily fluids, for example when the compliant bag 130 is porous and allows bodily fluids to enter into the internal void 134.

Figure 8:
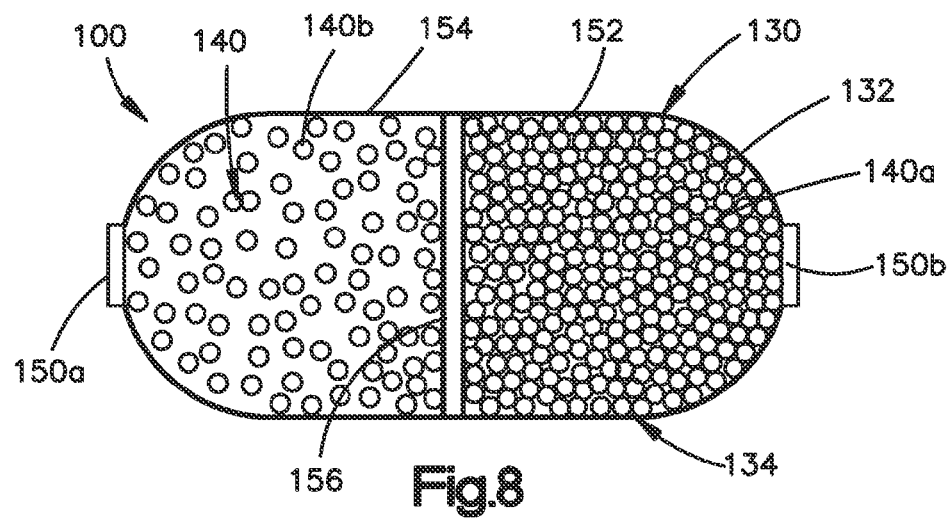
FIG. 8 is a side elevation view of the compliant bag of the intervertebral implant illustrated in FIG. 2A, including first and second separated chambers.

In accordance with one embodiment, the first type 140a of fill particles 140 can be disposed in the internal void 134 at a location anterior with respect to the second type 140b of fill particles 140 when the implant 100 is disposed in the intervertebral space 11. For instance, referring now to FIG. 8, the compliant bag 130 can include a plurality of chambers, such as at least a first chamber 152 and a second chamber 154, that is spaced from the first chamber 152. The compliant bag 130 can further include a partition 156 that separates the first chamber 152 from the second chamber 154. The compliant bag 130 can further include a first port 150a that is disposed at the first chamber 152 and configured to introduce fill particles 140, such as the first type 140a of fill particles, into the first chamber 152 and remove fill particles 140 from the first chamber 152 in the manner described above. The compliant bag 130 can further include a second port 150b that is disposed at the second chamber 154 and configured to introduce fill particles 140, such as the second type 140b of fill particles, into the second chamber 154 and remove fill particles 140 from the second chamber 152 in the manner described above. The compliant bag 130 can further include a fluid, such as the first and second fluids as described above, that are disposed in the first and second chambers 152 and 154, respectively. The first chamber 152 can be disposed anterior with respect to the second chamber 154, or can be alternatively positioned as desired, for instance posterior with respect to the second chamber 154. Alternatively still, as illustrated in FIG. 9A, the implant assembly 135 can include a plurality of bags 130 can be disposed between the superior and inferior endplates 110 and 120 and may or may not be coupled to each other. The bags 130 can be selectively filled with different types 140a and 140b of fill particles 140 as described above. Alternatively or additionally, at least one of the compliant bags 130 can contain a second compliant bag 130a that is disposed in the compliant bag 130. The second compliant bag 130a can be constructed in accordance with any embodiment described herein with respect to the compliant bag 130, and can include at least a second plurality of fill particles 140a that can be the same or different types of particles than the fill particles 140 disposed in the compliant bag 130. The port 150a of the second compliant bag 130a can be aligned with a port 150 of the compliant bag 130, such that the insertion instrument can extend through the port 150 of the compliant bag 130 and can engage the port 150a of the second compliant bag 130a so as to inject the fill particles 140 into the internal void 134 of the second compliant bag 130a.

The compliant bag 130 can be disposed between and coupled to the pair of endplates 110 and 120 that are configured to engage the inner surface 13a, which can be the inferior surface, of the superior vertebral body 12a, and the inner surface 13a, which can be the superior surface, of the inferior vertebral body 12b, respectively. The endplates 110 and 120 can be made from any of a variety of biocompatible metal or plastic materials known to the art. The implant 100 can further include at least one or more securement members 177 that project out from respective vertebral body-facing surfaces 111 and 121 of the endplates 110 and 120, and are configured to engage the inner surfaces 13a and 13b of the vertebral bodies 12a and 12b, respectively, so as to secure the position of the implant 100 within the intervertebral space 11. For instance, the seccurement members 177 can be configured as spikes, keels, bumps, rough surfaces, rails, teeth, screws, clamps, pins, and the like. The compliant bag 130 can be attached to the endplates 110 and 120 in any manner as desired. For instance, the compliant bag 130 can be sewed, weaved, knit, glued, welded, screwed, stalked, clamped, wounded, or the like, to the first and second endplates 110 and 120 as desired. In accordance with another embodiment, the compliant bag 130 can be integral with the endplates 110 and 120.

In accordance with one embodiment, the vertebral body-facing surfaces 111 and 121, respectively, of the superior and inferior endplates 110 and 120 can further include anti repulsion members such as teeth, spikes, surface texturing, grooves, microstructures, rails, pins, scales, or one or more keels, and can be formed from stainless steel, titanium and titanium alloys, ceramics, bone or artificial bone, or other biocompatible metals or polymers such as PEEK. The endplates 110 and 120 can define any respective geometry as desired so as to fit a corresponding variety of desired locations and anatomies. For a total disc replacement, the endplates desirably cover as much of the inner surfaces 13a and 13b of the vertebral body endplates 12a and 12b, respectively, as desired.

During operation, and with continuing reference to FIGS. 10A-B, an access corridor is formed to the intervertebral disc space 11 that is to receive the intervertebral implant 100. The implant 100 is inserted into the disc space 11 in a first profile configuration in which no or a small amount of fill particles 140 are enclosed within the compliant bag 130. Thus, the implant 100 has a first height H3 (FIG. 10A) along the transverse direction T. The implant assembly 135 can further include an insertion tube 171, such that the implant 100, including the compliant bag 130, is inserted through the tube 171 into a location between the first and second vertebral bodies 12a and 12b.

Once the surgeon determines that the implant 100 is properly positioned with respect to the adjacent vertebral bodies 12a and 12b, the insertion instrument 160 is connected to the implant 10, and in particular to the compliant bag 130, for instance via the port 150, and the fill particles 140 are delivered to the internal void 134 of the compliant bag 130 in the manner described above. In accordance with one embodiment, the fill particles are inserted into the compliant bag 130 to a sufficient volume of fill particles 140 such that natural motion of the removed disc is restored by providing articulation and rotation between the superior and inferior outer surfaces 131 and 133, respectively, of the compliant bag 130, and thus also between the superior and inferior endplates 110 and 120, while providing sufficient load bearing support and restoring disc height.

Thus, the fill particles 140 are inserted into the compliant bag 130 until the compliant bag defines a second height H4 (FIG. 10B) along the transverse direction that is greater than the first height H3. Alternatively, the fill particles 140 can be inserted into the internal void 134 of the compliant bag 130 until the compliant bag 130 reaches the second height H4 prior to implanting the implant 100, including at least the compliant bag 130, between the first and second vertebral bodies 12a and 12b. The fill particles 140 can be delivered to the internal void 134 of the compliant bag 130 in a sufficient amount such that the fill particles 140 are not attached to each other but interact during natural motion of the spine so as to provide an amount of resistance to the motion due to the friction encountered between adjacent ones of the fill particles 140 as they touch (e.g., rub or slide against) one another, for instance as the endplates 110 and 120 rotate relative to each other or translate relative to each other, or for instance as the superior and inferior surfaces 131 and 133, respectively, of the compliant bag 130 rotate relative to each other or translate relative to each other. It should be appreciated that the exterior surfaces of at least some up to all of the fill particles 140 can be rough (e.g., not smooth), so as to induce increase levels of friction as they rub or slid against each other, thereby tuning a level of resistance to rotation or translation of the superior and inferior surfaces 131 and 133 relative to each other.

It should be appreciated that the compliant bag 130 does not have a fixed center of rotation as the superior and inferior endplates 110 and 120 rotate and angulate relative to each other, and as the superior and inferior surfaces 131 and 133 of the compliant bag 130 rotate and angulate relative to each other. Thus, the fill particles 140 can engage each other so as to provide resistance, but in some embodiments not prevent, against rotation of the superior and inferior surfaces 131 and 133, and thus of the endplates 110 and 120, for instance about a transverse axis, and alternatively or additionally about an axis that is angularly offset with respect to the transverse axis. Thus, compliant bag 130 can provide a first resistance to relative rotation of the superior and inferior surfaces 131 and 133, and thus the endplates 110 and 120, when the bag 130 has a first volume of fill particles 140 in the internal void 134, and can provide a second resistance to relative rotation of the superior and inferior surfaces 131 and 133, and thus the endplates 110 and 120, that is greater than the first resistance when the bag 130 has a second volume of the fill particles 140 in the internal void 134 that is greater than the first volume.

The compliant bag 130 may alternatively be filled with the fill particles 140 to a sufficient volume such that the implant 100 provides less flexibility. The compliant bag 130 may be filled to such a point either intraoperatively or at a later time during a subsequent procedure. Thus, the compliant bag 130 can be filled with a first volume of fill particles 140 that causes the implant 100 to have a first flexibility, and can alternatively be filled with a second volume of fill particles 140 that causes the implant 100 to have a second flexibility that can be less than the first flexibility. For instance, the second volume of fill particles 140 can be greater than the first volume of fill particles. Alternatively or additionally, the first chamber 152 (FIG. 8) of the compliant bag 130 can be filled with a first volume of fill particles 140 that causes the first chamber to have a first flexibility, and the second chamber 154 (FIG. 8) can be filled with a second volume of fill particles 140 that causes the second chamber to have a second flexibility that can be less than the first flexibility. For instance, the second volume of fill particles 140 can be greater than the first volume of fill particles. It should be further appreciated that the fill particles of the first chamber 152 can move to the second chamber 154 during operation, and that the fill particles of the second chamber 154 can move to the first chamber 152 during operation.

Referring now to FIG. 11A, in accordance with one embodiment, the intervertebral implant 100 includes one or more compliant bags 130 as described above, but does not include the endplates 110 and 120. Accordingly, the complaint bag 130 can be inserted into the intervertebral space 11, and the fill particles 140 can be injected into the compliant bag 130 so as to increase the height of the compliant bag as from the first height H1 to the second height H2 as described above with reference to FIGS. 5A-B. When the compliant bag 130 has the second height H2, the compliant bag can contact the inner surfaces 13a and 13b of the vertebral bodies 12a and 12b. In such an embodiment, the position of the implant 100 can be secured by attaching, such as sewing, suturing, screwing, or staking, the compliant bag 130 directly to one or both of the adjacent vertebral bodies 12a and 12b. The superior outer surface 131 and the inferior outer surface 133 can include one or more securement members, as described above with respect to securement members 177, that can be configured as spikes, teeth, keels, fins, rough coatings, glue, coatings (bioactive or not) so as to provide primary and secondary fixation, and can further promote bony ongrowth or ingrowth.

In an alternate embodiment, the implant 100 can provide a nucleus, or intervertebral disc, replacement implant that includes the compliant bag 130 and the plurality of fill particles 140 as described above. The nucleus replacement implant, in accordance with one embodiment, does not include the superior and inferior endplates 110 and 120, and is insertable through a small window formed through the annulus fibrosus of the intervertebral disc subsequent to a partial or full nucleotomy. Once the implant 100 is inserted into the interior of the intervertebral disc, the fill particles 140 can be delivered into the internal void 134 of the compliant bag 130 until the desired rigidity/flexibility and height of the implant 100 is provided. In a first illustrative embodiment, the compliant bag 130 is filled to a point at which the bag 130 can articulate and rotate. For instance, as illustrated in FIG. 11B, where the intervertebral disc 167 is not removed, an incision 163 can be made through the annulus wall 165 of the intervertebral disc 167, so as to allow the implant 100 to be inserted in the intervertebral disc through the incision 163 when the compliant bag 130 defines the first height H1 as illustrated in FIG. 5A. Once the compliant bag 130 is disposed in the intervertebral disc 167, the fill particles can be injected into the internal void 134 as illustrated in FIG. 4 so as to increase the height of the compliant bag 130 to the second height as illustrated in FIG. 5B.

Figure 12:
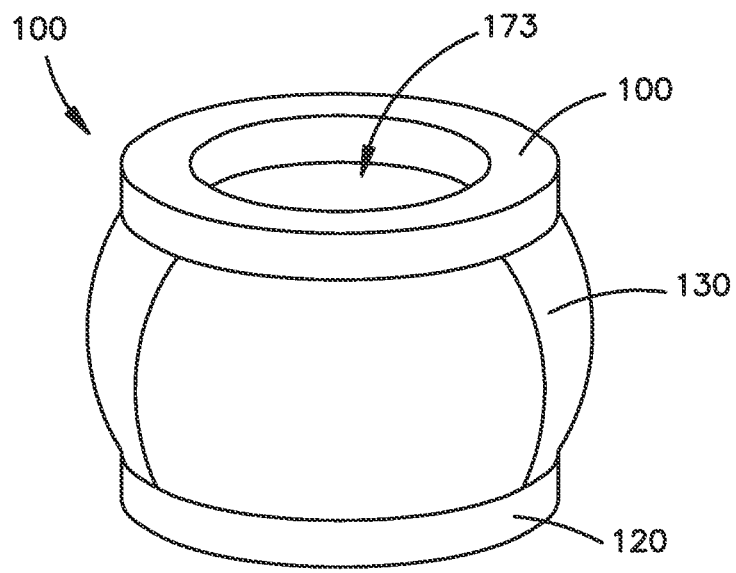
FIG. 12 is a perspective view of an intervertebral implant similar to the implant illustrated in FIG. 2A, but defining an aperture that extends transversely through at least one of the endplates.

In accordance with one embodiment, the implant 100 can be configured to allow fusion between the adjacent vertebral bodies 12a and 12b, for instance by providing the implant 100 without at least one or both of the superior and inferior endplates 110 and 120. Alternatively or additionally, as illustrated in FIG. 12, the implant 100 can define an aperture 173 that extends transversely through at least one or both of the endplates 110 and 120. For instance, a central portion of one or both of the endplates 110 and 120 can define the aperture 173, thereby leaving annular, for instance ring-like, endplates 110 and 120. The aperture 173 provides a path for fusion to occur between the compliant bag 130 and the corresponding one or both of the respective vertebral bodies 12a and 12b. Alternatively or additionally, the implant 100 can be configured to allow fusion between the adjacent vertebral bodies 12a and 12b, for instance by including a porous bag 130 to allow boney ingrowth or ongrowth, the inclusion of an amount of cement interior to the compliant bag 130 in addition to the fill particles, inclusion of allograft fill particles, and the like.

Figure 13:
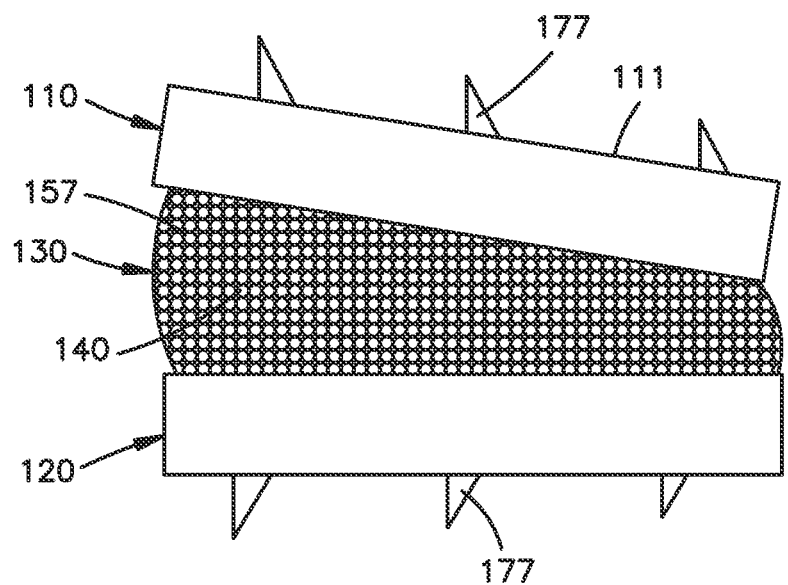
FIG. 13 is a side elevation view of an intervertebral implant similar to the implant illustrated in FIG. 3, but showing a cement disposed inside the internal void.

For instance, referring to FIG. 13, the implant 100 can include any volume of cement 157 as desired that can be injected into the internal void 134 so as to stiffen the compliant bag 130. For instance, the cement 157 can fix certain ones up to all of the loose discreet fill particles 140 to one another to provide a single fixed mass interior to the compliant bag 130. Such a procedure can be accomplished within the same surgical procedure as the implantation procedure or during a subsequent surgical procedure. In accordance with one embodiment, the cement 157 can be selectively inserted into a portion of the internal void 134, such as one of the chambers 152 and 154.

In yet another alternate embodiment, and as described above, the intervertebral implant 100 can be configured as a total disc replacement implant that can be provided without one or both of the superior and inferior endplates 11 and 120. In such a case, primary fixation mechanisms, such as spikes, keels, rails, pins, grooves, scales, and/or various microstructures may be disposed on the portions of the exterior surface of the compliant bag 130 configured for bearing against the adjacent vertebral bodies.

It will be appreciated by those skilled in the art that changes could be made to the embodiments described above without departing from the broad inventive concept thereof. It should further be appreciated that structural features and methods associated with one embodiments can be incorporated into other embodiments. It is understood, therefore, that this invention is not limited to the particular embodiments disclosed, but it is intended to cover modifications within the spirit and scope of the present invention, for instance as defined by the claims.

The invention claimed is:

1. An expandable intervertebral implant assembly configured for insertion along an insertion direction into an intervertebral space defined between a superior vertebral body and an inferior vertebral body, the expandable intervertebral implant comprising:
    a superior endplate configured for disposition adjacent to the superior vertebral body;
    an inferior endplate spaced from the superior endplate along a transverse direction that is substantially perpendicular to the insertion direction, the inferior endplate configured for disposition adjacent to the inferior vertebral body;
    at least one securement member that projects from at least one of the superior and inferior endplates along the transverse direction, the at least one securement member configured to engage the respective superior and inferior vertebral bodies; and
    a compliant bag coupled between the superior and inferior endplates, the compliant bag including an outer wall, the outer wall defining a superior coupling surface and an inferior coupling surface spaced from the superior coupling surface along the transverse direction, the superior coupling surface coupled to the superior endplate, the inferior coupling surface coupled to the inferior endplate, the outer wall further defining an internal void, the internal void of the compliant bag configured to receive a plurality of discrete particles therein so as to expand the implant along at least the transverse direction from a first configuration into second expanded configuration,
    wherein when 1) the expandable implant is disposed between the vertebra bodies, 2) the plurality of discrete particles are received in the internal void, 3) the expandable implant is in the second expanded configuration, and 4) the at least one securement member is engaged with the respective at least one of the first and second vertebral bodies, the expandable implant provides a resistance to relative rotation of the superior and inferior endplates with respect to each other about at least a transverse axis that is substantially aligned with the transverse direction.

2. The expandable intervertebral implant assembly of claim 1, wherein when the particles are disposed in the internal void and the superior and inferior endplates are secured to the respective superior and inferior vertebral bodies, the implant provides a resistance to a relative translation of the superior and inferior endplates with respect to each other along a direction that is perpendicular to the transverse axis.

3. The expandable intervertebral implant assembly of claim 1, wherein the at least one securement member is a plurality of securement members.

4. The expandable intervertebral implant assembly of claim 1, wherein at least one securement member is disposed on the superior coupling surface of the bag, and another securement member is disposed on the inferior coupling surface of the bag.

5. The expandable intervertebral implant assembly of claim 1, wherein the compliant bag further includes a first region and a second region that is spaced from the first region along one of the transverse direction or a second direction that is angularly offset with respect to the transverse direction, wherein the second region of the compliant bag is constructed to have a different strength, rigidity, or flexibility than the first region.

6. The expandable intervertebral implant assembly of claim 1, wherein the compliant bag is a first compliant bag, wherein the implant further comprises at least a second compliant bag that is disposed in the internal void of the first compliant bag.

7. The expandable intervertebral implant assembly of claim 6, wherein the first compliant bag includes a first port extending at least partially through the outer wall, and wherein the second compliant bag includes a second outer wall that defines a second internal void, and a second port extending at least partially through the second outer wall of the second bag, wherein the second port is aligned with first port such that an instrument can be inserted through the first port to be at least partially received by the second port.

8. The expandable intervertebral implant assembly of claim 1, wherein the fill particles are rigid.

9. The expandable intervertebral implant assembly of claim 1, further comprising an instrument configured to deliver the plurality of fill particles into the internal void.

10. The expandable intervertebral implant assembly as recited in claim 9, further comprising a port that extends at least partially through the outer wall of the compliant bag wherein the instrument is configured for insertion at least partially through the port so as to deliver the plurality of fill particles to the internal void.

11. The expandable intervertebral implant assembly of claim 9, wherein when coupled to the first and second vertebral bodies provides 1) a first resistance to relative rotation of the superior and inferior surfaces with respect to each other about the transverse axis when the internal void has a first volume of fill particles, and 2) a second resistance to relative rotation of the superior and inferior surfaces with respect to each other about at least the transverse axis when the internal void has a second volume of fill particles that is greater than the first volume, wherein the second resistance to relative rotation is greater than the first resistance to relative rotation.

12. The expandable intervertebral implant assembly as recited in claim 1, wherein the plurality of fill particles are inserted into the internal void prior to inserting the intervertebral implant into the intervertebral space.

13. The expandable intervertebral implant assembly as recited in claim 1, wherein the plurality of fill particles are inserted into the internal void after inserting the intervertebral implant into the intervertebral space.

14. The expandable intervertebral implant assembly as recited in claim 1, wherein the fill particles have smooth exterior surfaces.

15. The expandable intervertebral implant assembly as recited in claim 1, wherein the fill particles have rough exterior surfaces.

16. The expandable intervertebral implant assembly as recited claim 1, defining an aperture that extends through at least one of the inferior and superior endplates so as to promote fusion of the compliant bag with a respective vertebral body.

17. The expandable intervertebral implant assembly as recited in claim 1, wherein the compliant bag defines first and second chambers separated by a partition.

18. The expandable intervertebral implant assembly as recited in claim 1, further comprising second and third compliant bags that are disposed between the superior and inferior endplates, each of the second and third compliant bags defining an internal void that is configured to receive respective pluralities of fill particles.

19. The expandable intervertebral implant assembly as recited in claim 1, wherein the plurality of fill particles further comprises a first type of fill particles and a second type of fill particles that are different than the first type of fill particles.

20. The implant assembly as recited in claim 19, wherein the compliant bag defines a first chamber that contains the first type of fill particles, and a second chamber that contains the second type of fill particles.

* * * * *